US010258484B2

(12) United States Patent
Pressacco et al.

(10) Patent No.: US 10,258,484 B2
(45) Date of Patent: Apr. 16, 2019

(54) INSTRUMENT FOR THE REMOVAL OF A BONE INSERT AND CORRESPONDING METHOD

(71) Applicant: LIMACORPORATE S.P.A., San Daniele del Friuli (UD) (IT)

(72) Inventors: Michele Pressacco, Udine (IT); Simone Ursella, Mijano (IT); Christoph Fiedler, Diekhof (DE); Paul D. Paterson, Amherst, NY (US)

(73) Assignee: LimaCorporate S.P.A., San Daniele del Friuli (UD) (IT)

( * ) Notice: Subject to any disclaimer, the term of this patent is extended or adjusted under 35 U.S.C. 154(b) by 394 days.

(21) Appl. No.: 14/303,433

(22) Filed: Jun. 12, 2014

(65) Prior Publication Data

US 2015/0359544 A1 Dec. 17, 2015

(51) Int. Cl.

*A61B 17/16* (2006.01)
*A61F 2/46* (2006.01)
*A61B 17/14* (2006.01)

(52) U.S. Cl.

CPC ........ *A61F 2/4612* (2013.01); *A61B 17/1617* (2013.01); *A61B 17/147* (2016.11); *A61B 17/1684* (2013.01)

(58) Field of Classification Search

CPC ............... A61F 2/4612; A61B 17/1617; A61B 17/1642; A61B 17/1684

See application file for complete search history.

(56) References Cited

U.S. PATENT DOCUMENTS 3,702,611 A * 11/1972 Fishbein ............ A61B 17/1666 408/154
4,475,852 A * 10/1984 Koppelmann ........ B23B 51/102 408/159
5,015,255 A * 5/1991 Kuslich ............. A61B 17/1671 128/898
7,429,264 B2 * 9/2008 Melkent ............ A61B 17/1617 606/159
8,034,088 B2 * 10/2011 Pagano ................ A61B 17/025 606/279
8,343,158 B2 * 1/2013 Birkbeck ........... A61B 17/1617 606/80

(Continued)

*Primary Examiner* — Matthew J Lawson

(74) *Attorney, Agent, or Firm* — Hickman Palermo Becker Bingham LLP; Malgorzata A. Kulczycka

(57) ABSTRACT

The invention relates to an instrument and a corresponding surgical method for the removal of a bone insert, for example for a shoulder prosthesis. The instrument is of the type comprising:

- a stem-like body (40) extending along a longitudinal axis (x-x) and provided with a proximal grip and a distal operating head (15) slidably associated with the stem-like body (40) for movement towards and away from each other;
- a cutting element (30) inside said operating head; and
- an end tip (16) protruding coaxially from said operating head. The following is also provided:
- a pushing mechanism (8), inserted inside said operating head and acting on said cutting element so as to displace it angularly from a rest position, where it is concealingly housed inside said end tip, to an operative position where it projects through a side opening in the end tip; said cutting element having an end extending substantially in a direction transverse to said longitudinal axis when in the operative position.

14 Claims, 17 Drawing Sheets

9
39
35
38
8
40
7
18
O
31

(56) References Cited

U.S. PATENT DOCUMENTS

| | | | | |
|---|---|---|---|---|
| 8,696,672 | B2 * | 4/2014 | Barnhouse | A61B 17/1671 606/79 |
| 2001/0034526 | A1 * | 10/2001 | Kuslich | A61B 17/1617 606/80 |

* cited by examiner

INSTRUMENT FOR THE REMOVAL OF A BONE INSERT AND CORRESPONDING METHOD

The present invention relates to an instrument for the removal of a bone insert intended, for example, for a reverse or anatomical shoulder prosthesis.

The principles of the present invention are applicable to various operational requirements, but the description which follows is provided with more specific reference to the treatment of different degrees of erosion of the glenoid cavity following a trauma or a pathology affecting the shoulder, without this however implying any limitation of the Applicant's rights.

From the content of the attached claims it will become clear that the scope of protection of the present invention extends to surgical applications intended for the removal of bone inserts in areas of the skeleton not limited to the example of the humeral head.

FIELD OF APPLICATION

As is well known, the humerus is a long bone of the upper limbs and is the main element in the skeletal structure of the arm since the other long bones of the upper limbs, namely the radius and the ulna, are anatomically speaking considered to form part of the forearm.

The humerus comprises a long body, called the diaphysis, and two opposite ends called the epiphyses, i.e. proximal epiphysis and distal epiphysis. The proximal epiphysis is articulated with the scapula forming a scapulo-humeral articulation, while the distal epiphysis is articulated with the two bones of the forearm, i.e. the radius and the ulna.

The head of the humerus, namely the proximal epiphysis, has a large smooth hemispherical surface which is lined with a cartilage and is seated in a glenoid cavity of the scapula. The head is bounded at the bottom by the both anatomical and surgical neck of the bone.

It should also be noted that at the bottom of the anatomical neck, in the front part of the bone, there is a forwards facing protuberance known as the lesser tubercle (also called trochin) inside which a subscapularis muscle is inserted. At the top and laterally with respect to the lesser tubercle there is the greater tubercle (called trochiter) which, with its three faces, allows the insertion of other muscles of the so-called rotator cuff.

Over and above these anatomical details, for the purposes of the present invention, it should be pointed out that the glenohumeral joint allows a large degree of movement of the upper limb necessarily to the detriment of the stability. Thus the anatomical system must ensure the right balance between mobility and stability, something which makes the glenohumeral joint prone to clinical instability. The instability is a pathological condition which is manifested in the form of acute pain associated with an excessive displacement of the humeral head inside the glenoid cavity during the active movement of the shoulder.

Static and dynamic factors play a complex and cooperative part in maintaining the articular stability. In-depth studies have established that there exists a certain instability factor when erosions are present in the glenoid cavity.

More particularly, it has been established that there essentially three different morphologies of the glenoid cavity, which may be classified as follows:

concave morphologies, which represent about 54% of the cases and are characterized by a small degree of central wear and a central dome;

biconcave morphologies, which represent 42% of the cases and are characterized by a rear peripheral wear with more or less partial rear dislocation;

retroverse morphologies, which are less common and take the form of an excessive retroversion of the glenoid cavity by more than 25°, normally of dysplastic origin.

Studies carried out on patients with arthrosis have showed that in glenoid cavities with non-concentric arthropy and rear erosion there is a high complication rate which adversely affects the stability and biomechanics of the articulation.

However, these problems may be solved surgically by attempting to restore the stability and biomechanics of the articulation so as to eliminate the pain from which the patient is suffering.

In order to restore the correct stability and biomechanics parameters as well as achieve renewed mobility with elimination of the pain, a reverse or anatomical total prosthesis, as appropriate, may be conveniently used.

A prosthesis is an artificial joint or articulation, made of metal or plastic, which resembles in form the glenohumeral articulation.

The prostheses normally comprise both a humeral prosthetic component and a glenoid component and, in so-called reverse prostheses, these components are substantially reversed compared to an anatomical total prosthesis.

PRIOR ART

In order to restore optimally the biomechanics of the articulation, the erosion and the angle of the glenoid cavity must also be rectified in some way. One of the operative techniques envisages the possibilities of using bone implants instead of metal implants.

These implants, in the case of a first implant, may be obtained from the head of the humerus which must in any case undergo resection in order to make space for the humeral component of the prosthesis.

For example, in the case of reverse prostheses, in which there is a glenoid component terminating in a concave articular surface, the presence of a bone insert between the glenoid cavity and the prosthesis is envisaged.

A surgical technique which envisages the removal and implant of a bone insert is for example described in detail in French patent application No. 2,916,961 in the name of Tornier.

Although advantageous in various respects and substantially meeting needs, the surgical technique described in that document has a major drawback relating to the operating step where a bone insert is removed from the head of the humerus.

The bone insert in question, which is removed from the head of the humerus, is used to complete the structure of the prosthesis on the glenoid cavity side since it is arranged between the convex end portion of the glenoid component of the prosthesis and a seat specially prepared inside the articular cavity so as to form a bone callus for consolidating in situ the prosthesis.

The insert is suitably removed from the head of the humerus which, as mentioned, must in any case undergo resection by the surgeon in order to seat the concave humeral component of the reverse prosthesis, while ensuring compatibility and preventing any risk of rejection.

The step of core-boring or drilling the bone insert and subsequent removal thereof by means of a lateral cut performed in the head of the humerus are carried out before the same bone insert may be attached to its prosthesis component.

This means that the bone insert must be handled after its removal or must in any case be placed to one side pending completion of the other surgical steps necessary for preparing the glenoid cavity, with the potential risk of bacterial contamination.

Moreover, the operating steps for boring and removal of the insert are objectively complex and demanding for the surgeon and involve the use of a large number of specific instruments which also result in the removal of a quantity of bone material far greater than that which would be strictly necessary for completion of the steps for preparing insertion of the prosthesis.

Finally, it must also be commented that the surgical technique proposed by the prior art for removal of the bone insert is relatively inefficient from the point of view of the sequence of operating steps which are necessary for completion of the operation.

The present invention aims to overcome all these drawbacks by considering the technical problem of how to provide an instrument and corresponding surgical method able to allow the removal of a bone insert in a simpler and more efficient manner compared to the known solutions, while ensuring at the same time completely sterile handling of the insert.

SUMMARY OF THE INVENTION

The proposed solution forming the basis of the present invention is that of extracting or removing the bone insert to be removed by already associating it or attaching it to a portion of the relevant prosthesis component.

This basic idea also involves modification of the method of removal of the bone insert compared to the sequence of steps envisaged by the prior art.

On the basis of this proposed solution, the scope of which is understandably broader than that expressly implied with reference to the example of the anatomical or reverse shoulder prosthesis, the aforementioned technical problem is solved by an instrument for removal of a bone insert, for example for a shoulder prosthesis, of the type comprising:

- a stem-like body extending along a longitudinal axis (x-x) and provided with a proximal grip and a distal operating head;
- a cutting element inside said operating head; and
- an end tip projecting coaxially from said operating head, characterized in that it comprises further:
- a pushing mechanism, inserted inside said operating head and acting on said cutting element so as to displace it angularly from a rest position, where it is concealingly housed inside said end tip, to an operative position where it projects through a side opening in the end tip; said cutting element having an end extending substantially in a direction transverse to said longitudinal axis when in the operative position.

Advantageously, the cutting element is curved or has the form of a circle arc and comprises a widened proximal portion slidable inside a guide of matching shape formed in the operating head and a tapered end portion which is angularly movable between the rest position, where it is concealingly housed inside the end tip of the operating head, and the operative position, where it extends transversely projecting relative to the longitudinal axis.

The operating head has an essentially cylindrical shape and comprises a circular-rim guide inside which the cutting element is movably guided.

The distal portion of the operating head is slightly concave, while the end tip has a frustoconical form with a base diameter smaller than the diameter of the operating head and projecting coaxially with the longitudinal axis from the distal portion.

It should be noted that the pushing mechanism also comprises a resilient element which constantly biases said cutting element towards said rest position.

Moreover, the pushing mechanism comprises a distal end of the stem acting on the cutting element.

In greater detail, the pushing mechanism is such that the stem is slidable inside said operating head with a predefined longitudinal stroke so that its distal end acts on said cutting element against the action of spring-loaded means; sliding of the stem is obtained by means of an advancing and retracting movement engaged on a perimetral portion.

The distal end of the stem has a circular cross-section and diameter smaller than the internal diameter of the operating head, while the spring-loaded means consist of a spring wound around the distal end of the stem.

The spring extends resiliently inside a variable-extension, cylindrical, annular gap which is defined between an inner edge of the operating head and an edge formed by the smaller diameter of the distal end of the stem.

The technical problem is also solved by a method for removing a bone insert intended, for example, for a shoulder prosthesis, of the type comprising the steps of:

- forming a hole of predefined diameter inside a bone portion from which said insert is to be removed;
- inserting inside said hole an operating end of an instrument provided with a cutting element;
- said cutting element being movably guided from a rest position, where it is concealingly housed inside said end, to an operative position, where it projects through a side opening in the said end, transversely relative to a longitudinal axis of the instrument;
- deep-cutting a base of said insert by rotating said instrument through 360 degrees;
- removing the instrument from said hole;
- inserting and fixing a pin element inside said hole;
- perimetrally milling an insert of predefined diameter by centering a milling cutter on said pin element;
- removing the insert and the pin element attached thereto.

The characteristic features and advantages of the instrument and the associated method according to the invention will emerge from the description of a non-limiting example of embodiment provided with reference to the accompanying drawings.

DETAILED DESCRIPTION

As already mentioned above, the instrument and the removal method according to the present invention, which will be described in detail below, are applicable to the removal of any bone insert, which could also be situated in the femoral iliac zone, without this involving any limitation of the Applicant's rights.

However, the attached drawings show in diagrammatic form the head portion of a bone along the human skeleton, for example the head of a humerus, as an example application of the instrument and the method according to the invention.

The removal method is described below with reference to a surgical technique applied to the implantation of a reverse total shoulder prosthesis shown in FIG. 1, but only by way of a non-limiting example and for the purpose of simplification of description of the invention.

Figure 1:
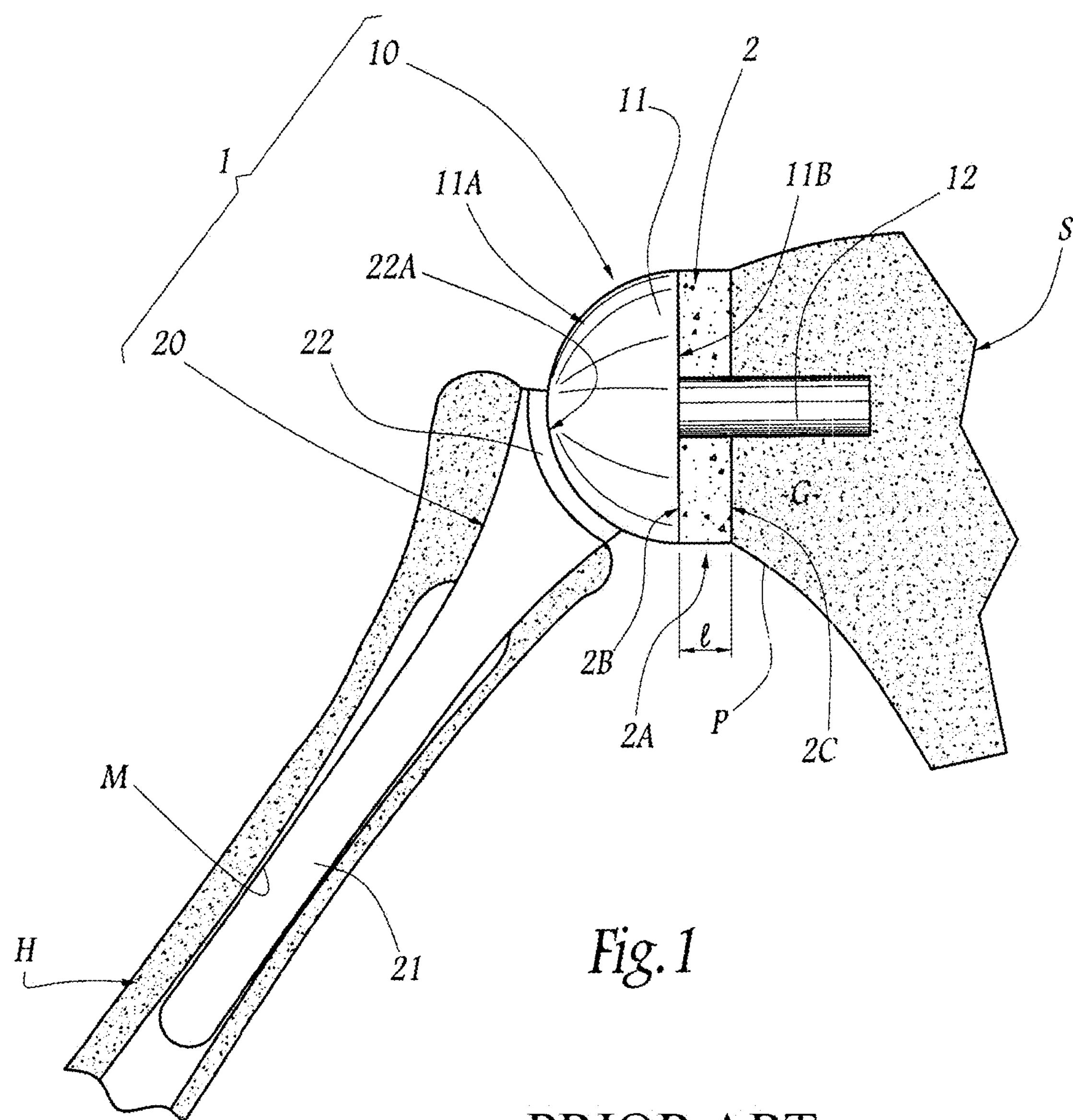
FIG. 1 shows a diagrammatic cross-sectional view of a reverse total shoulder prosthesis according to the prior art.

FIG. 1 shows in diagrammatic form a reverse total shoulder prosthesis 1 with an already known structure.

In the sector of total shoulder prostheses, reverse prostheses comprise, on one side, a glenoid component associated with the glenoid cavity G of a scapula S of a patient and terminating in a convex articular surface 11A and, on the other side, a component integrated in the humerus H defining a concave articular surface 22A; these two articular surfaces 11A, 22A, cooperating with each other, recreate the shoulder joint.

FIG. 1 shows a shoulder prosthesis 1 comprising a glenoid component or glenoid cavity and a humeral component, indicated by the numbers 10 and 20, respectively, and situated in the scapula S and in the humerus H of a patient. The glenoid component 10 comprises a head 11 which has, on the opposite side to the glenoid cavity G of the scapula S, an articular convex face 11A with a generally semispherical form and, on the side directed towards the glenoid cavity G of the scapula S, a flat face 11B. In the illustrative example shown in the figures, the face 11B is generally flat, but it may also have a more elaborate geometry and be for example substantially concave or convex.

The glenoid component 10 further comprises an anchoring stem 12 which extends transversely with respect to the projecting face 11B, in the opposite direction to the face 11A, and the free end of which is firmly anchored in the glenoid cavity G, thus ensuring joining of the glenoid component to the side of the scapula S. The shank 12 may be externally threaded or, in general, have a surface which favors anchoring. A bone insert 2 is arranged between the face 11B of the glenoid portion 10 of the prosthesis and the glenoid cavity G of the scapula S, said insert having a substantially cylindrical external shape, with a circular base, the external diameter of which is substantially the same as the diameter of the head 11.

The bone implant 2 to be associated with the glenoid component of the prosthesis is removed from the upper epiphysis of the humerus of the shoulder of the same patient. In this way the risk of rejection, poor biocompatibility or the potential transmission of diseases or infections is reduced.

Moreover, in this way advantageously also resection and forming of the head of the humerus which is suitable for engagement of the other humeral component of the reverse total prosthesis is obtained.

The humeral component 20 of the reverse prosthesis comprises a medullary stem 21 intended to be inserted inside the medullary cavity M of the humerus H. At the top end the stem 21 widens into a head 22 which has on its side opposite to the shank 21 a concave articular surface 22A with a semispherical form having a radius substantially the same as that of the convex surface 11A. When the prosthesis 1 is implanted, as shown in FIG. 1, the surfaces 11A and 22A are directed in contact against each other, allowing the various movements required by the shoulder.

Owing to the presence of the implant 2, the face 11A is situated at a predefined distance from the glenoid surface G and this arrangement is referred to, in the technical jargon of the sector, as induced "lateralization". Advantageously, the lateralization of the glenoid component of the prosthesis also induces an increase in the muscular tension of the rotator cuff. The glenoid and humeral prosthetic components are thus stabilized and therefore benefit from improved relative rotation and a better mobility without any longer the risk of a shoulder dislocation. Furthermore, the geometric centre of articulation of the prosthesis is situated correctly in the glenoid cavity.

Advantageously, according to the present invention, the surgical method and the instrument described here allow easier removal of the bone insert 2, for example both for a reverse prosthesis 1 of the shoulder, such as that described above, and for other types of operations which in any case require the removal of bone inserts from a patient.

Figures 2, 2A:
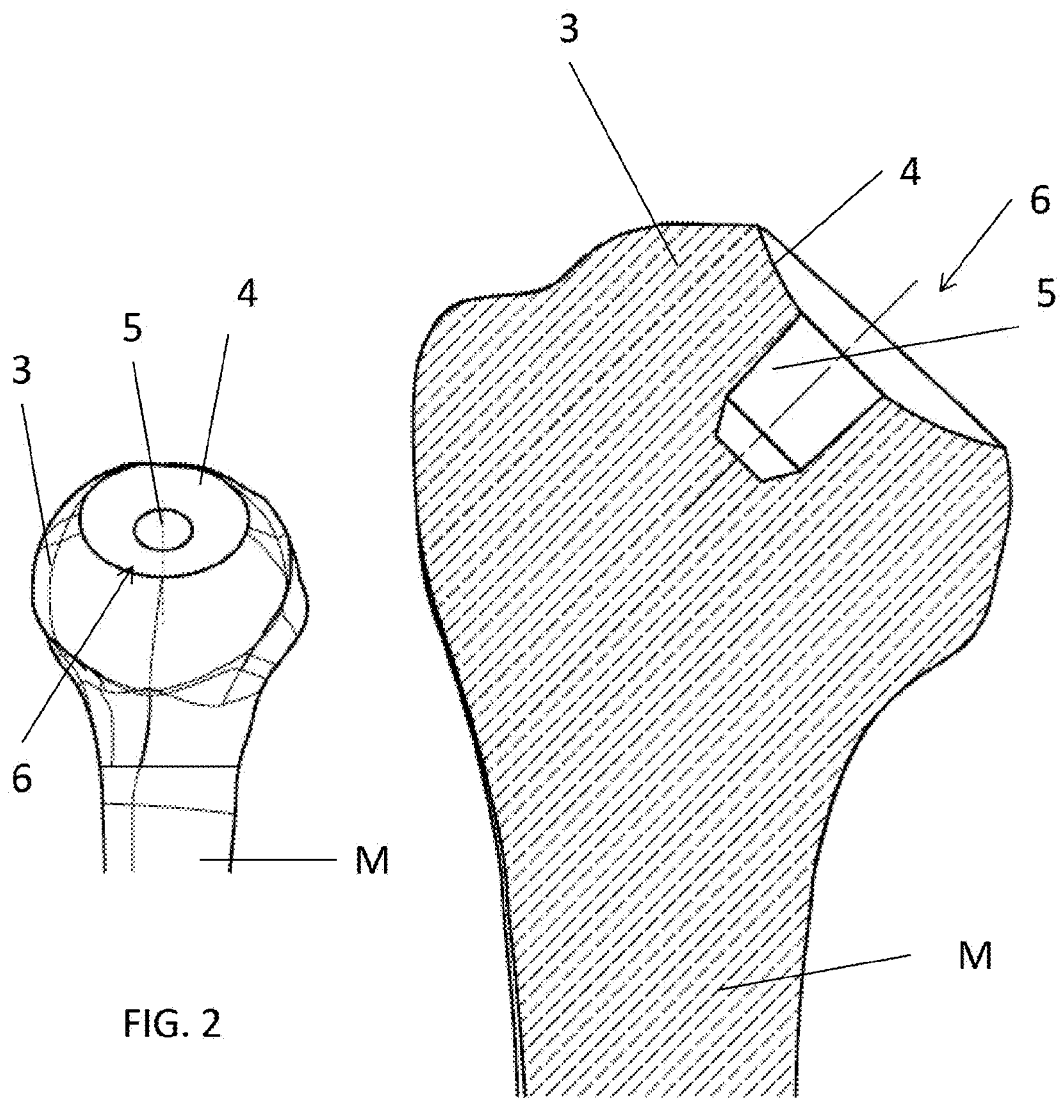
FIG. 2 shows a diagrammatic perspective view of a bone portion to which the method of the present invention is applied, for example the head of a humerus.
FIG. 2A is a diagrammatic longitudinally sectioned view of the bone portion according to FIG. 2.

The steps of the surgical method developed by the Applicant may be easily understood from the sequence shown in FIG. 2 onwards.

The description which follows does not intend to describe all the steps involved in the surgical treatment for removal of the bone insert 2, but only those steps which are most important and relevant to the description of the invention;

therefore, detailed explanations as to how the patient is positioned or how the head of the humerus or the glenoid cavity are surgically exposed will be omitted.

For the purposes of the present invention, the humeral epiphysis 3 undergoes firstly a milling operation to define a concave recess 4 which has substantially the shape of a spherical cup.

A central hole 5 of predefined diameter, in particular a hole with a frustoconical shape, is formed in the bottom of this recess 4.

Obviously, the person skilled in the art will understand that the shape of the hole 5 may be cylindrical if necessary.

The milling resection means for performing a resection in the humeral epiphysis and defining the concave recess 4 as well as the drilling means for centrally boring the hole 5 are of the conventional type and may be used in cooperation with a centering or guide stem (not shown in that conventional) which helps define the direction of application of these means for forming the hole 5 centered in the recess 4.

Similarly, the person skilled in the art will understand that the steps for forming the recess 4 and the hole 5 could also be reversed with the formation of the hole 5 which may precede the removal of the bone material from the humeral epiphysis until the concave recess 4 is obtained.

In any case, at the end of these first operating steps, the head of the humerus has a receiving seat 6 formed by the assembly of the hole 5 and concave recess 4 which is subsequently intended to house a pin element 25 visible in FIGS. 11 and 12. This pin element 25 comprises a flange 23, with shape matching that of the concave recess 4, and a pin 24 projecting centrally and intended to be inserted inside the hole 5.

Preferably the pin 24 has circular and longitudinal grooves for better anchoring of the pin element 25 inside the hole 5 and stabilization of the flange 23 inside the recess 4 of the receiving seat 6.

Figure 3:
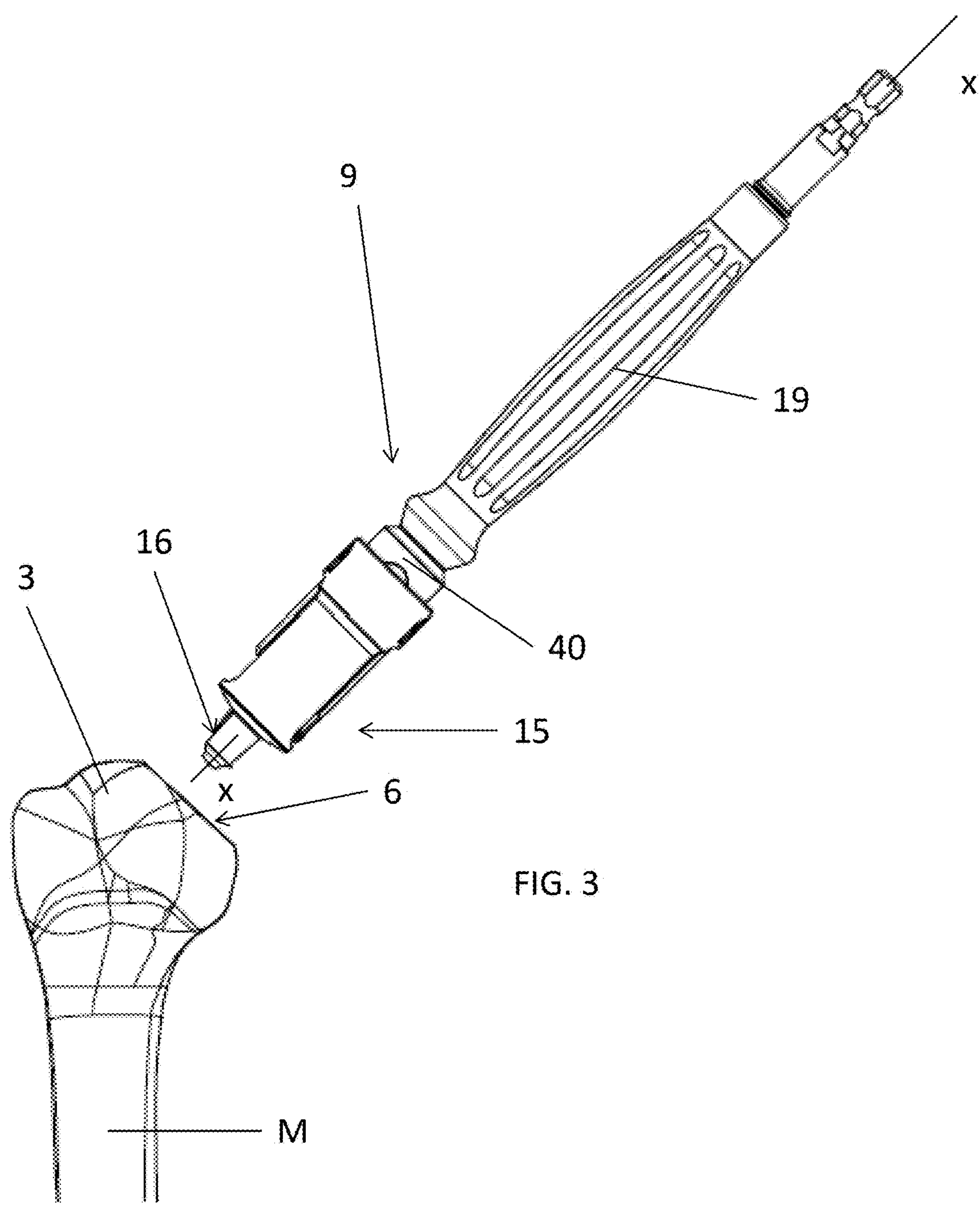
FIG. 3 shows a diagrammatic side view of an instrument provided in accordance with the present invention during approach towards a bone portion to be treated.

In accordance with the present invention, an instrument 9 is brought up close with its operating end 15 so that it may be inserted inside the seat 6, as shown in FIG. 3.

The internal structure of the instrument 9 can be seen from the cross-sectional view shown in FIGS. 4, 5, 6 and 8.

The instrument 9 comprises a stem-like body 40 extending along a longitudinal axis (x-x) and provided with a proximal grip and a distal operating head 15. The distal operating head is slidably mounted on one end of the stem 40 between a rest position and an operative position.

The operating head 15 is provided internally with a cutting element 30, in particular a blade having a predefined constant lateral thickness.

An end tip 16 projects coaxially from said operating head 15 and forms a kind of laterally open frustoconical bit.

The operating head 15 has internally a pushing mechanism 8 for acting on the cutting element 30 so as to displace it angularly from a rest position, where it is concealingly housed inside the end tip 16, and an operative position where it projects through a side opening 27 in the end tip.

The cutting element 30 has a blade 31 extending substantially in a direction transverse to said longitudinal axis x-x when it is in the operative position.

Figure 6:
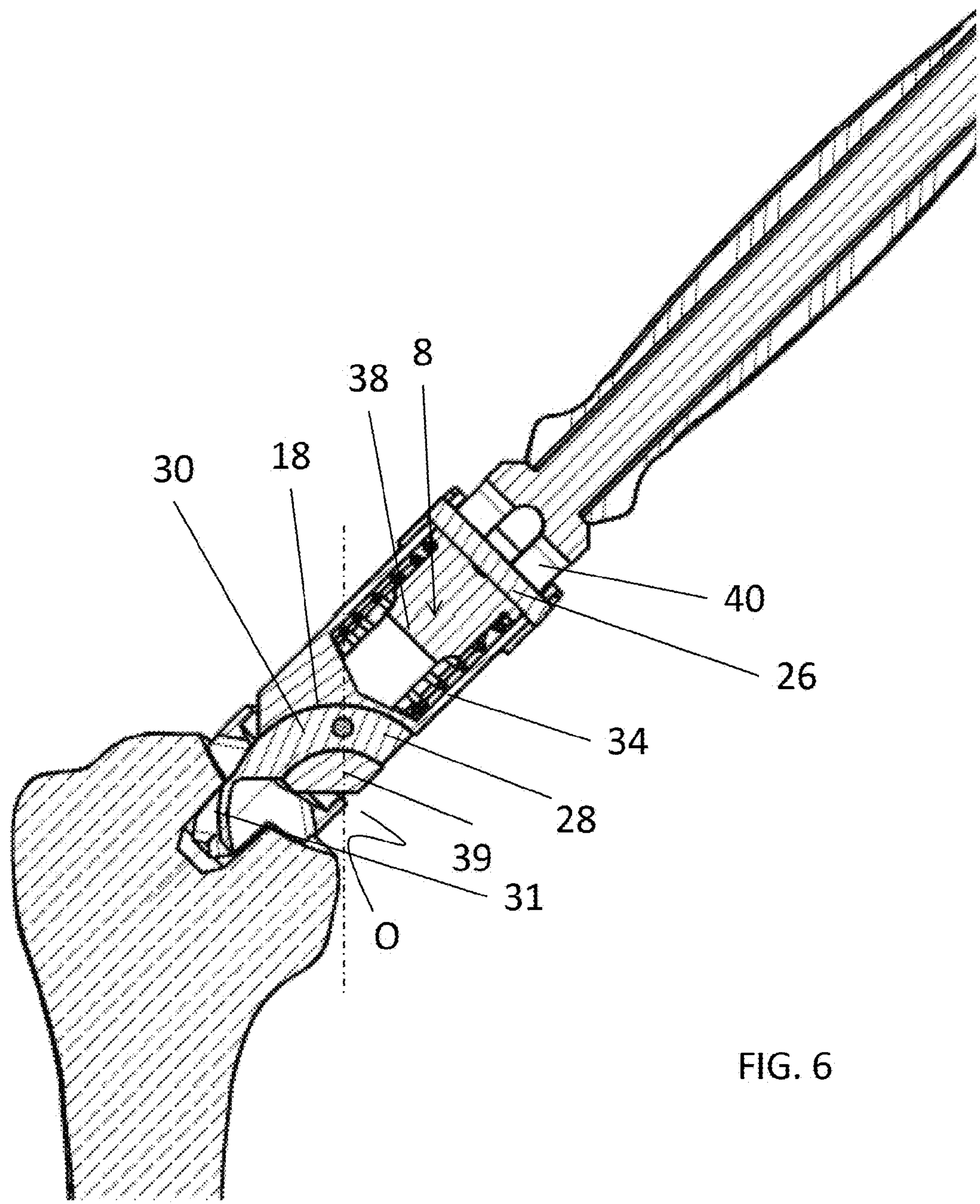
FIG. 6 shows a diagrammatic cross-sectioned side view, similar to that of FIG. 5, in which the instrument according to the present invention is at the start of an operating step.
Figure 7:
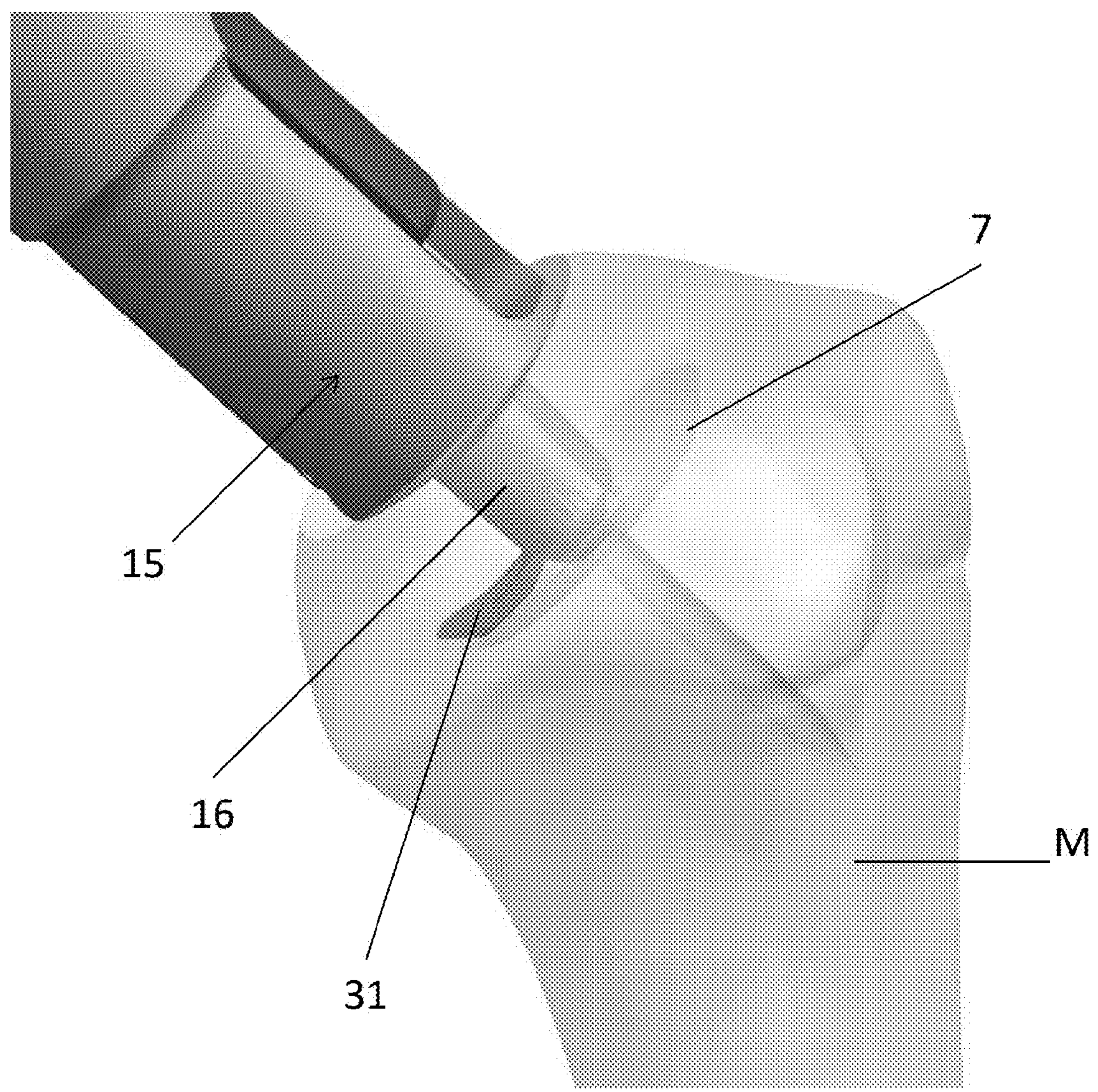
FIG. 7 shows a perspective picture view showing a portion of the instrument according to the invention during its operating step.
Figure 8:
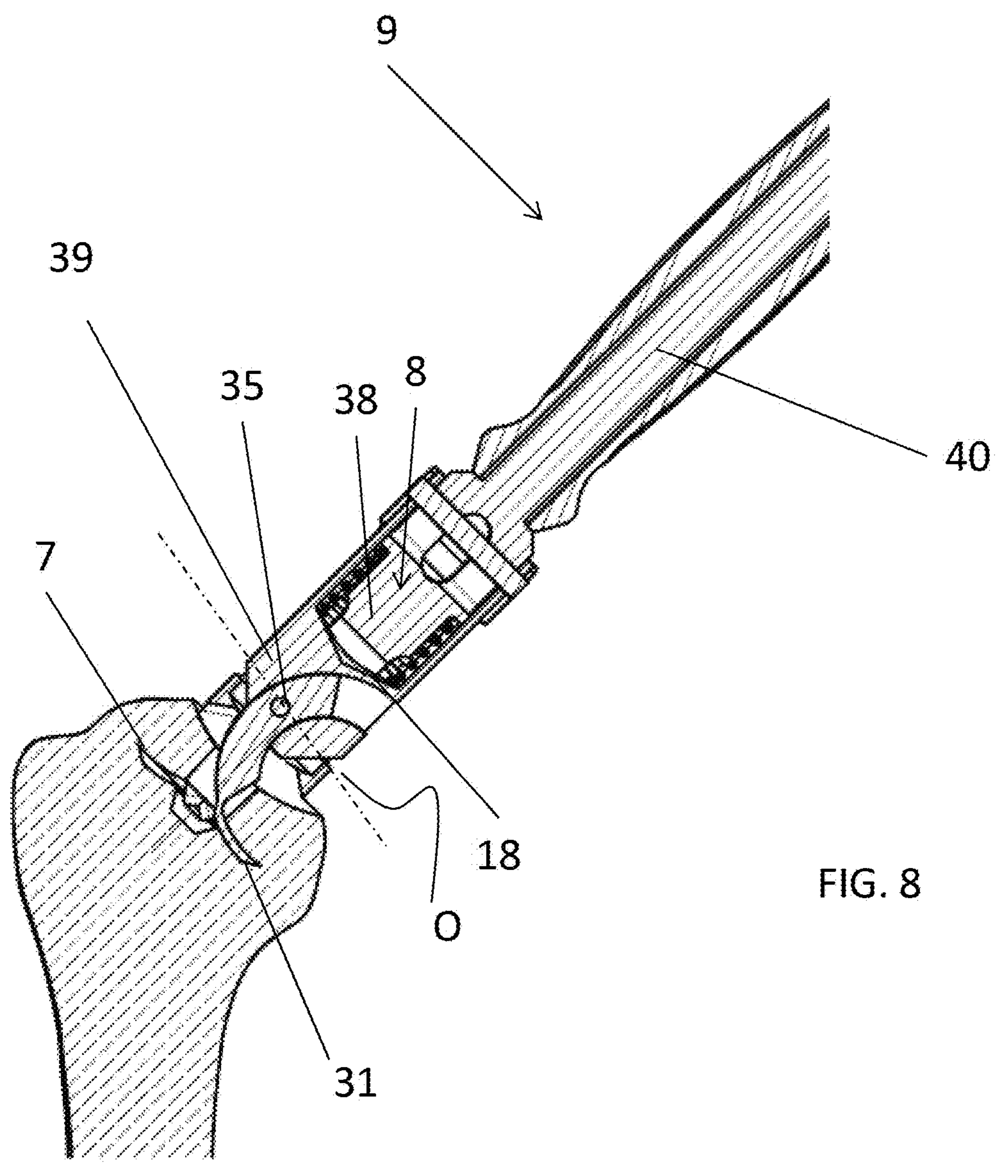
FIG. 8 shows a diagrammatic cross-sectioned side view of the instrument according to FIG. 7 during operation.

As is clearly shown in FIGS. 6, 7 and 8, when the blade 31 of the cutting element 30 starts to emerge through the side opening 27 of the end tip 16 it also starts to perform its incision function in the spongy part of the bone to be cut. As the end 31 performs its action, a cut 7 is formed and, following rotation of the instrument 9 through 360°, this cut assumes an essentially circular form.

The cutting element 30 is curved, essentially in the form of a semi-circle or circle arc, and comprises a widened portion 28, which extends over most of the circle arc and is slidable inside a guide 18 provided in the solid-material portion of the operating head 15, and a tapered blade 31, which is angularly movable between said rest position, where it is concealingly housed inside the end tip 16 of the operating head 15, and said operative position, where it extends transversely with respect to the longitudinal axis (x-x) in the manner of a sickle.

Figure 9:
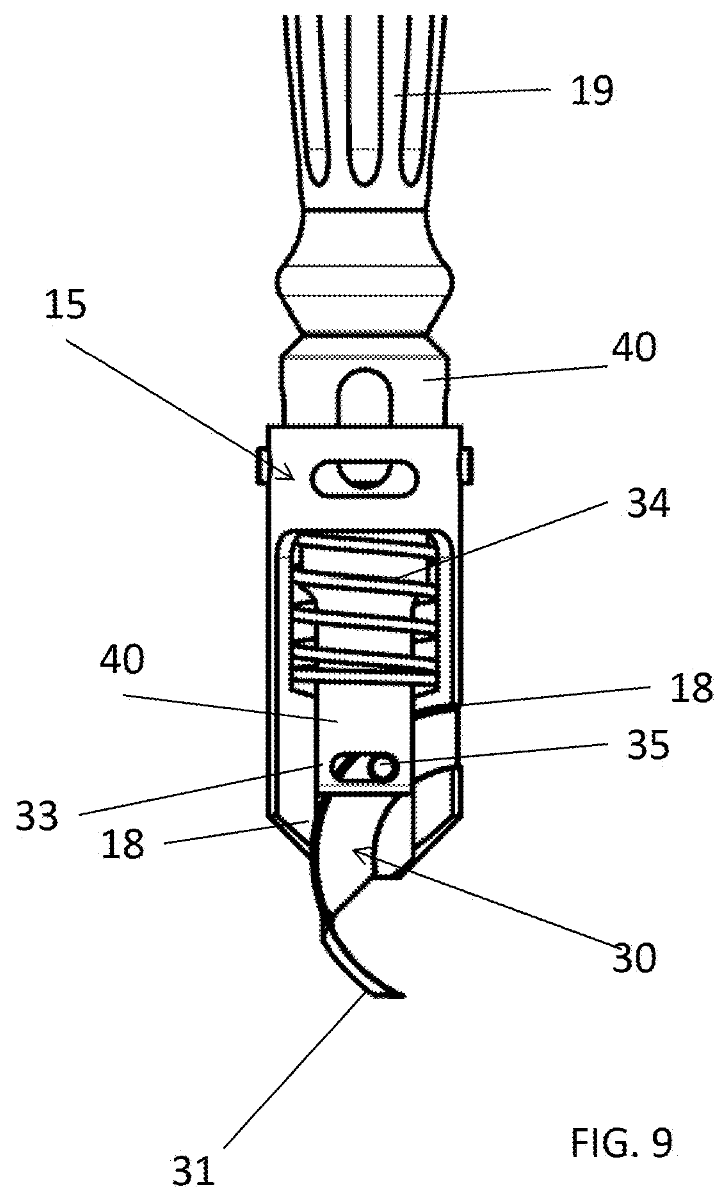
FIG. 9 shows a perspective view of a detail of the instrument according to the invention.

The widened proximal portion 28 is slidable inside the circular-rim guide 18 of matching shape formed in the operating head 15, thus moving angularly about a point of instantaneous rotation—diagrammatically indicated by O—which is also the centre of the curved cutting element 30 and the circular-rim guide 18. A pin 35 is also provided, integral with the cutting element 30, and extends perpendicularly with respect to the plane in which said cutting element 30 lies, as can be clearly seen in FIG. 9.

A guide slot 33, which is eyelet-shaped, is formed transversely with respect to the axis x-x on the distal end of the stem and is engaged by the pin 35 and acts on the said pin during displacement from the rest position to the operative position.

The operating head 15 has an essentially cylindrical shape and surrounds the pushing mechanism 8 and the distal end portion 8, which is preferably fork-shaped, of the stem 40.

The solid-material distal portion 39 of the operating head 15 is associated with the end tip 16 which is substantially the end part of a cylindrical shaped lid or cover with a frustoconical end tip 16, which covers both the distal end 38 of the stem 40 and the distal solid-material portion 39 of the operating head 15 so as to be formed integrally therewith.

Figure 4:
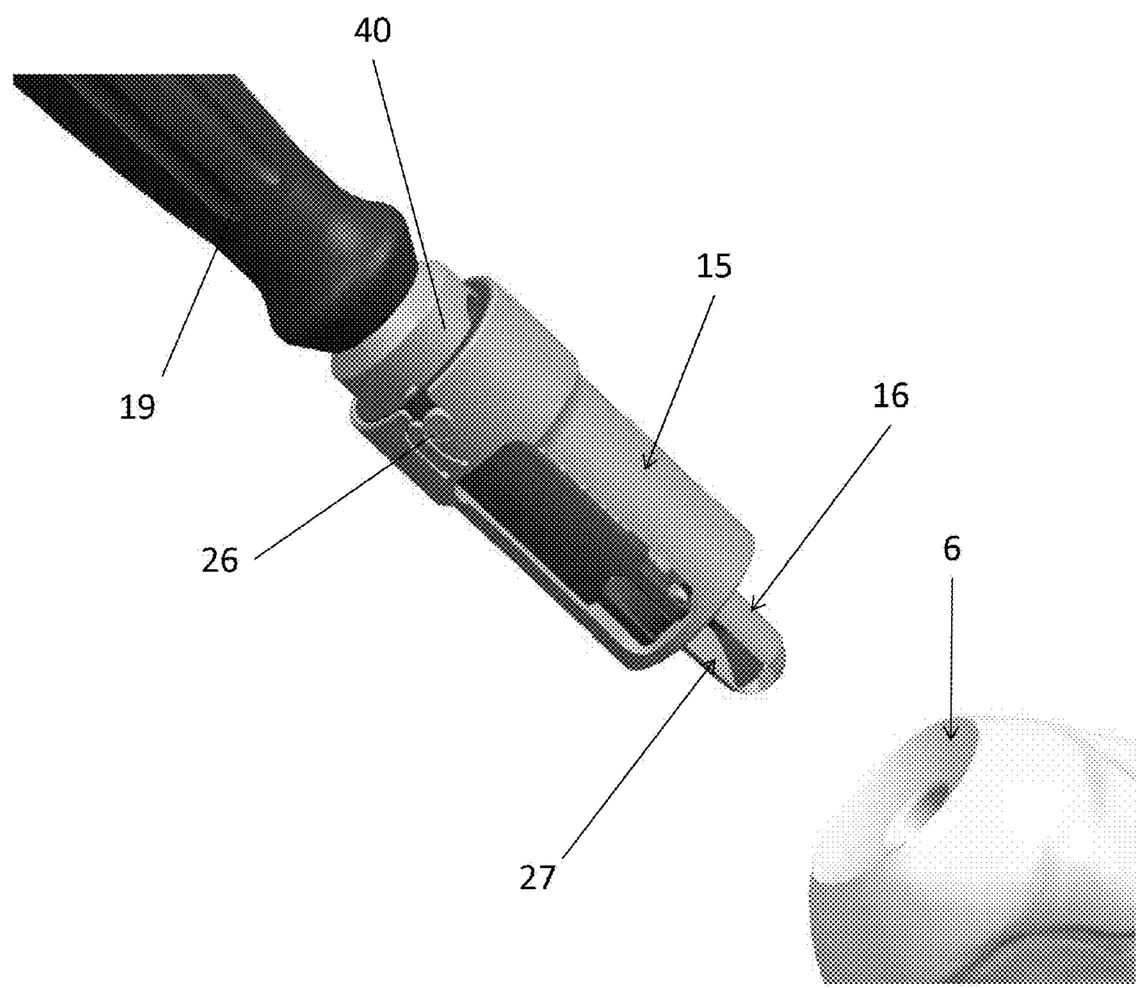
FIG. 4 shows a perspective picture view showing the instrument of the present invention before an operating step.
Figure 5:
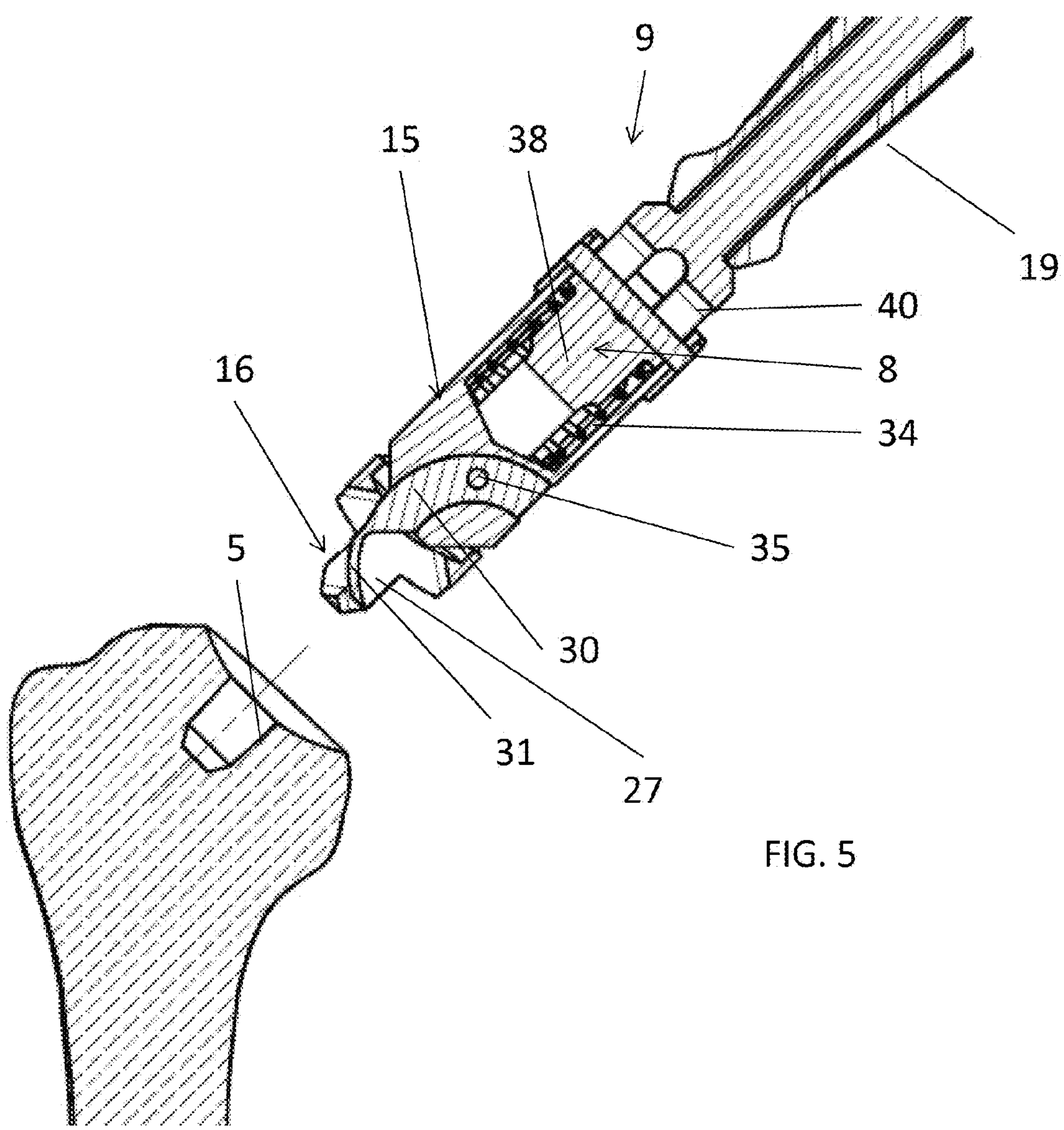
FIG. 5 shows a diagrammatic cross-sectioned side view of the instrument according to the present invention at the start of an operating step.

A pin 26 is provided projecting laterally from the operating head 15 so as to be snap-engaged by a deformable element formed in the cylindrical cover and visible in FIG. 4.

When the end tip 16 fixed to the operating head of the instrument 9 is inserted inside the hole 5, the distal surface of the operating head 15 comes into mating contact with the recess 4 of the seat 6 on the epiphysis of the humerus.

The pushing mechanism 8 also comprises a resilient element 34 arranged between the stem 40 and the operating head 15 and constantly biasing the stem 40 and the operating head 15 away from each other and therefore the cutting element 30 towards said rest position.

The side opening 27 in the end tip 16 is an opening extending along the entire longitudinal extension of the end tip, as shown in FIG. 7, so as to allow the blade 31 of the cutting element 30 to emerge fully.

The pushing mechanism 8, and in any case the distal end portion 38 of the stem 40, is slidable inside the operating head 15 with a predefined longitudinal travel. The fork-shaped distal end 38 of the stem 40 engages with the pin 35 via the guide slot 33 and therefore forces the cutting element 30 to slide inside its matching seat 18 against the action of the resilient means 34.

The distal end 38 of the stem 40 has a circular cross-section and diameter smaller than the internal diameter of the operating head 15 and has the function of receiving a section of the resilient element 34 and guiding it during the compression and release phase.

By means of the pushing or pressing force applied by the surgeon acting on the grip 19 of the stem 40 the blade 31 may be gradually made to protrude against the action of the resilient recall means 34, so that the resection action occurs gradually with rotation of the instrument through 360°.

Once the blade 31 has completed, acting in the manner of a sickle, the operations for resection of the deep base of the bone insert 2, thus performing the circular cut 7, the instrument 9 may be removed, releasing the resilient means which perform their elastic recall action 34 recalling the cutting element 30 inside the end tip 16 of the operating head 15.

In this way, the instrument is free again and may be removed.

Figure 10:
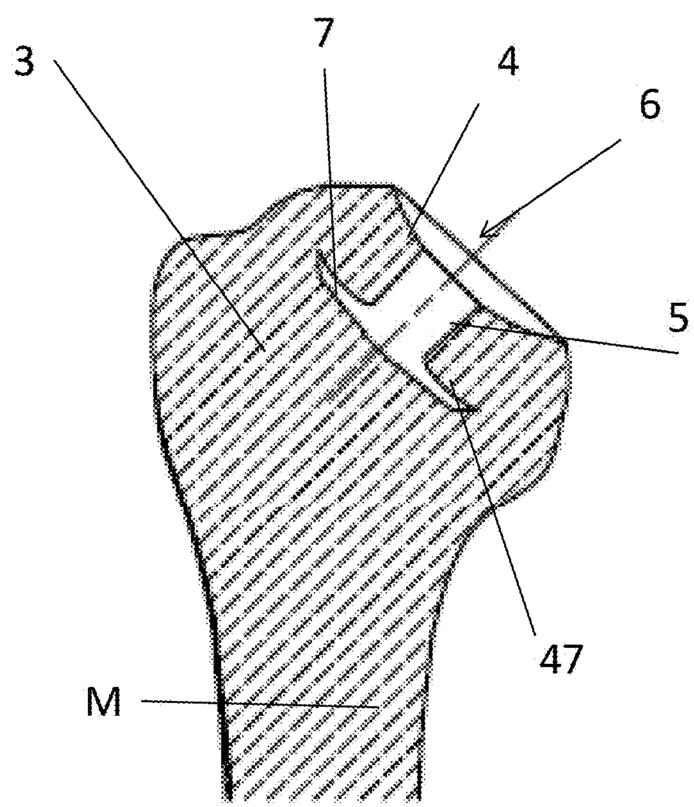
FIG. 10 shows a longitudinally sectioned view of a detail of the bone according to FIG. 2, in which a deep cut has been made using the instrument according to the invention.

The end portion 3 of the bone M which is operated on for removal of the inert 2 has a cross-section as shown in FIG. 10 where a deep base 47 of the insert 2 has been defined by means of a circular cut 7.

Figure 11:
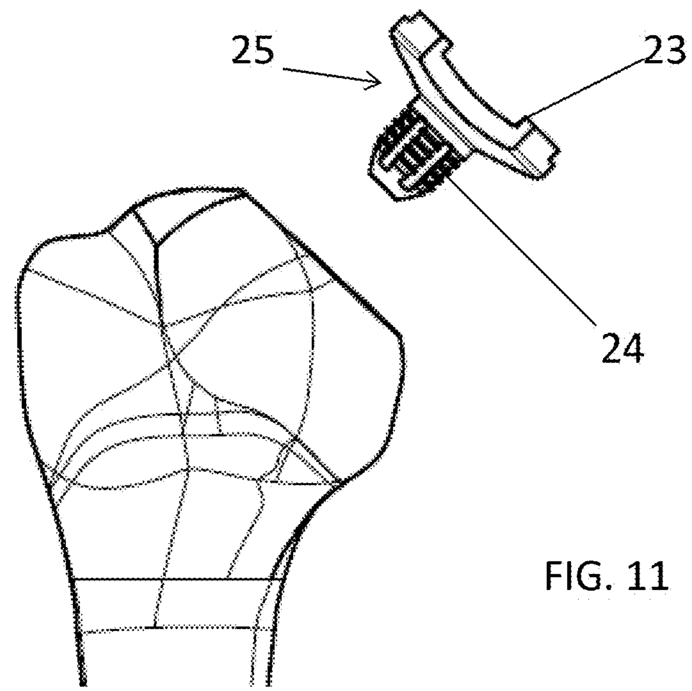
FIG. 11 shows a diagrammatic perspective view of a detail of the bone according to FIG. 2 in which a prosthesis component is about to be inserted.
Figure 12:
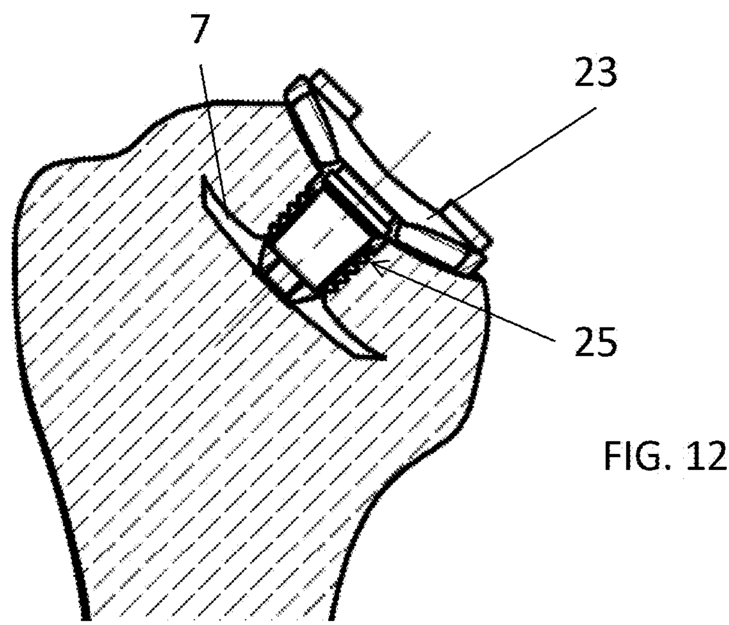
FIG. 12 shows a longitudinally sectioned view in which the prosthesis portion according to FIG. 11 has been inserted in the bone portion according to FIG. 2.

At this point it is possible to insert the pin element 25—also called "metal back"—which has an engaging portion 24 with perimetral grooves and is inserted by means of an interference fit inside the hole 5 until the flange makes bearing contact inside the matching recess 4 of the seat 6, as clearly shown in FIGS. 11 and 12.

The flange 23 has holes for stabilizing bone screws.

Thereafter the method according to the invention envisages successive terminal operative steps, some of which may be defined as being optional.

Figure 13:
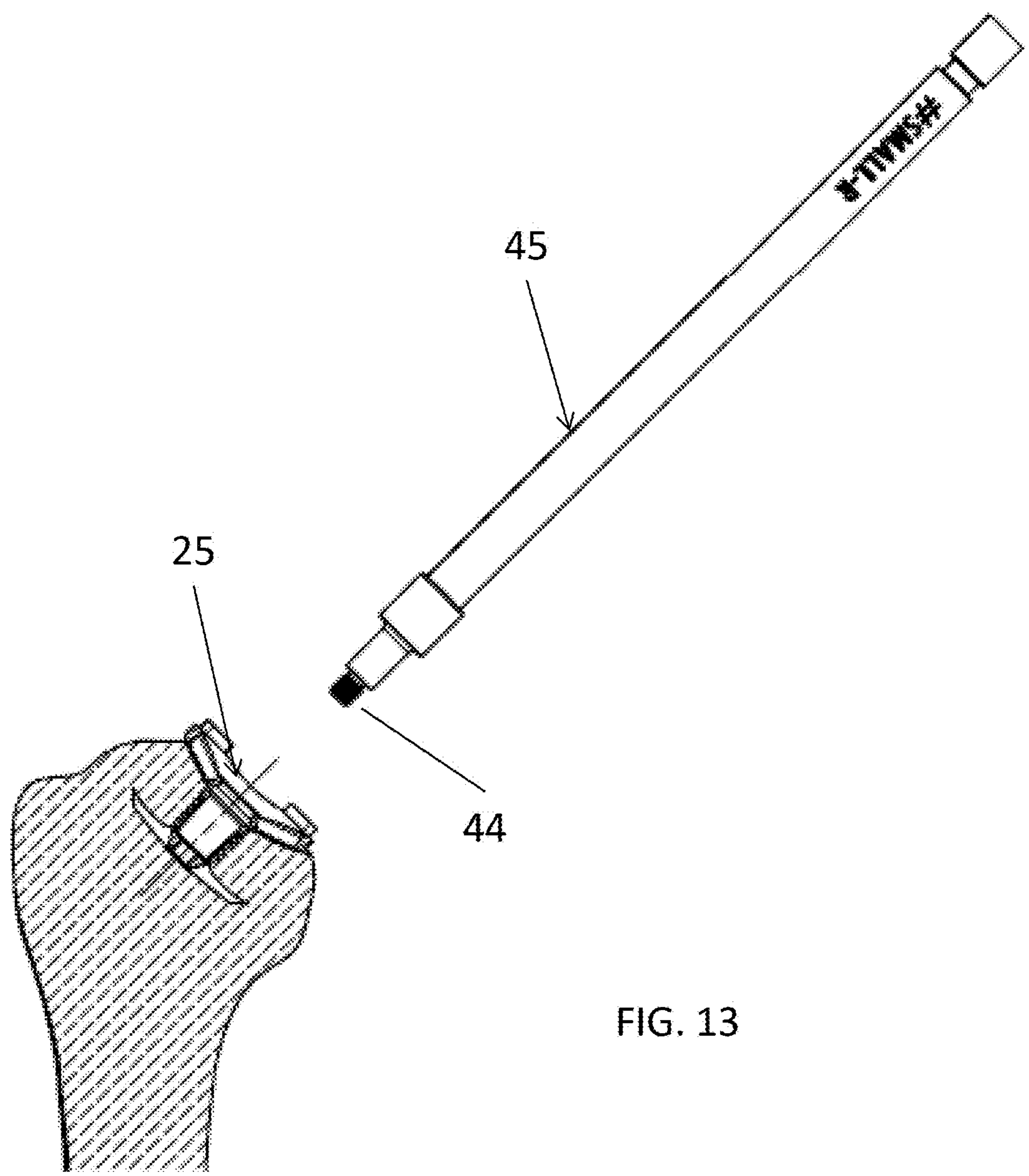
FIG. 13 shows a partially sectioned diagrammatic view of the bone portion according to FIG. 2 undergoing successive operating steps of the method according to the invention.
Figure 14:
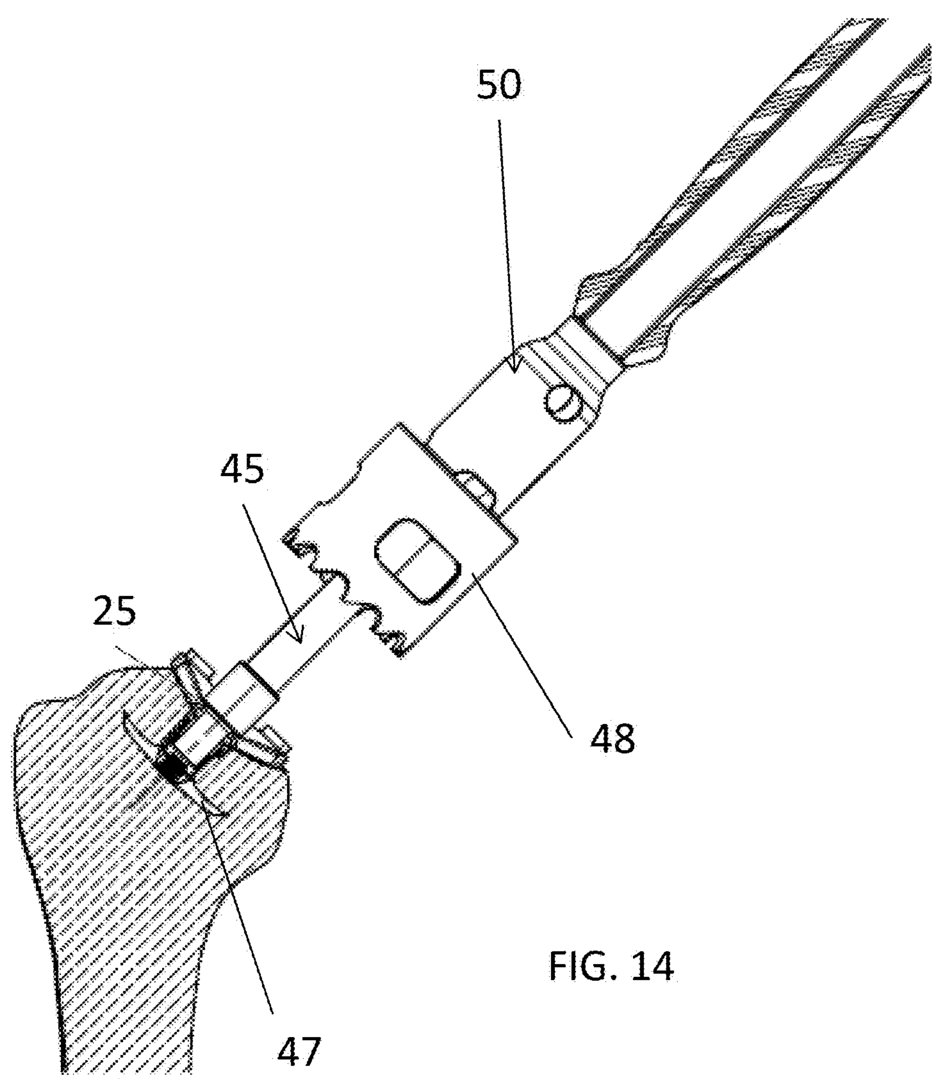
FIGS. 14 and 15 show respective partially sectioned diagrammatic views of operating steps of the method according to the invention.

For example, FIG. 13 shows a guide rod 45 which has a threaded end 44 inserted inside the pin element 25.

The pin 24 is internally hollow and has a thread inside which the aforementioned end 44 of the guide rod 45 may be engaged.

This guide rod acts as a guide for a milling cutter 50 provided with an end tool 48 with an essentially circular shape designed to perform core-boring of the insert 2 around the flange 23.

Figure 15:
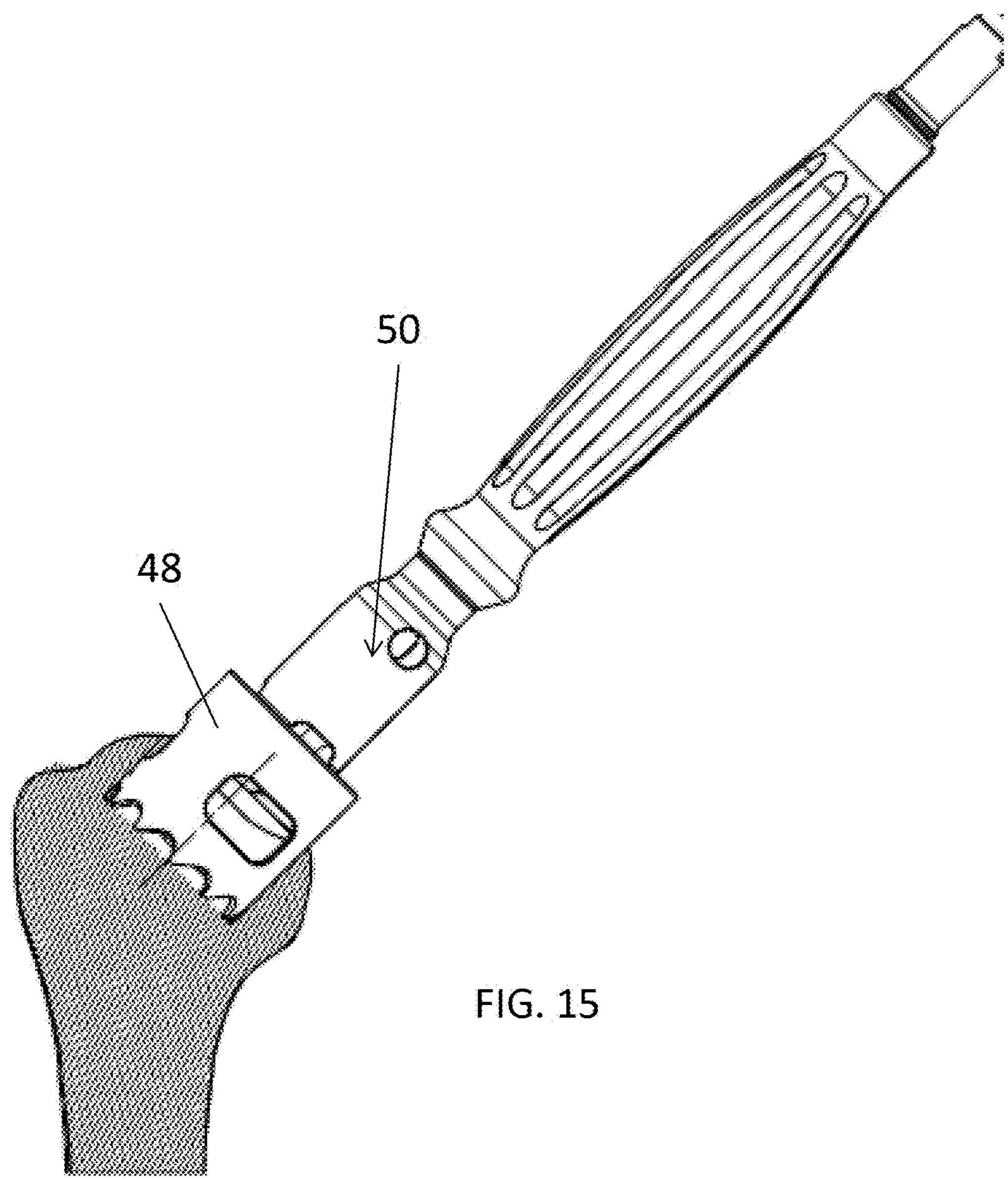
Figure 16:
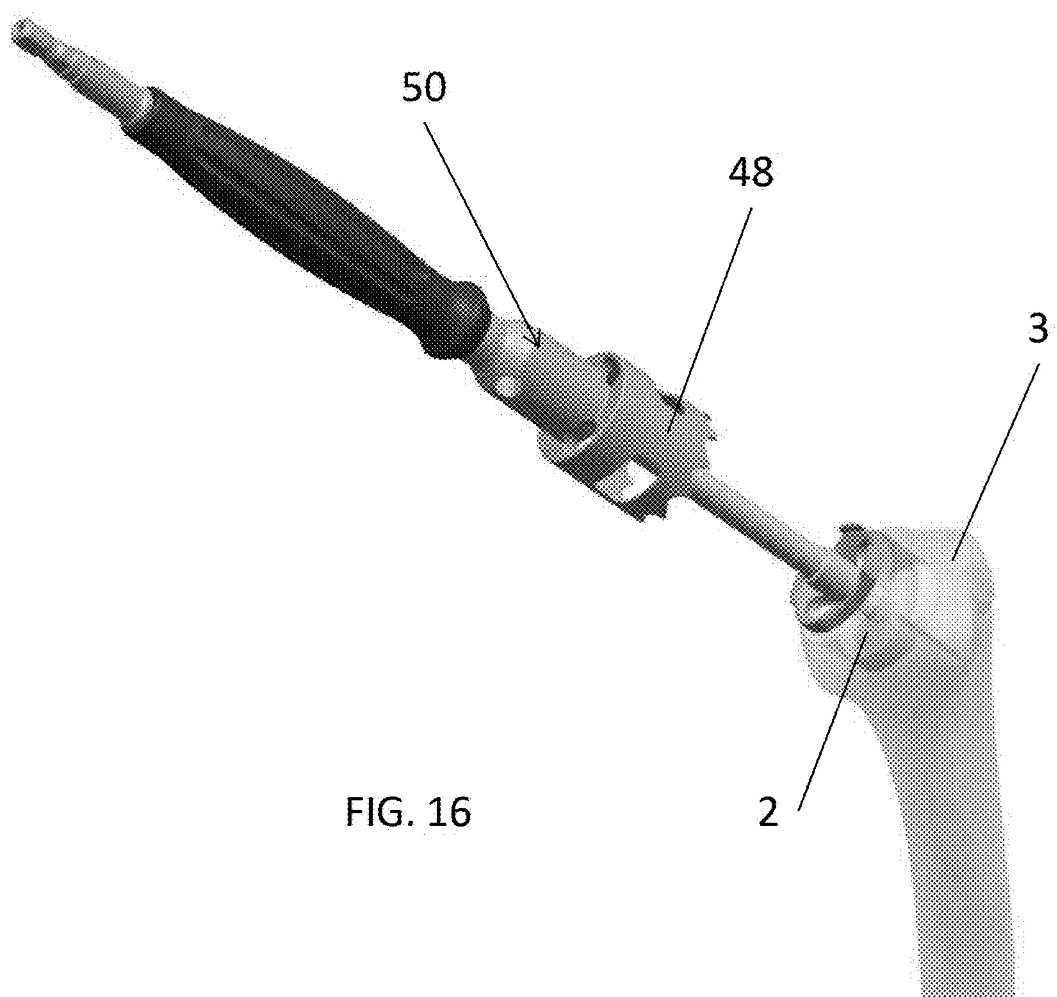
FIG. 16 is a perspective picture view of the example shown in FIG. 15 from a different view point.

FIG. 15 shows diagrammatically the action performed by the tool 48 of the milling cutter 50 on the head of the humerus M.

The perimetral milling or core-boring operation produce a cylindrical cut 43 which penetrates deep as far as the circular cut 7. In this way the insert 2 is easily resected from the surrounding bone material and may be easily removed by means of a suitable removal instrument.

The milling cutter 50 is then removed and an extractor 55 with a gripping head 54 is used to remove the insert 2 thus cut. As clearly shown in FIG. 18, the extractor 55 is in turn guided along the guide rod 45 which is still fastened to the pin element 25. The gripping head 54 is snap-engaged with the flange 23 of the pin element 25 and the insert attached to the pin element 25 may be removed.

More particularly, the extractor 55 of the metal back 25 snap-engages onto the guide rod 45. The head 54 enters inside the screw holes of the flange 23 of the metal back 25 in order to stabilize the rotational movement about the axis of the extractor and therefore allow directional adjustment of the implant.

The operating steps which allow removal of the bone insert 2 from the portion 3 of bone H may be summarized extremely succinctly as follows:

- forming a hole 5 of predefined diameter inside a bone portion from which the insert 2 is to be removed;
- inserting inside the hole 5 the operating end 16 of the instrument 9 provided with a cutting element 30;
- the cutting element 30 being movably guided from a rest position, where it is concealingly housed inside the end tip 16 of the operating head 15, to an operative position, where it projects through a side opening 27 in the said end tip 16, transversely with respect to a longitudinal axis x-x of the instrument 9;
- deep-cutting a base of the insert 2 by rotating the instrument 9 through 360°, as is clearly shown in FIG. 7;
- removing the instrument 9 from the hole 5;
- inserting and fixing a pin element 25 inside said hole 5;
- perimetrally milling the insert 2 of predefined diameter by centering a milling cutter 50 on said pin element 25;
- removing the insert 2 and the pin element 25 attached thereto.

The fact that the seat 6 also comprises the surface recess 4 is entirely optional. Obviously, this surface recess 4 may advantageously receive the flange 23 attached to the pin 25

Figure 17:
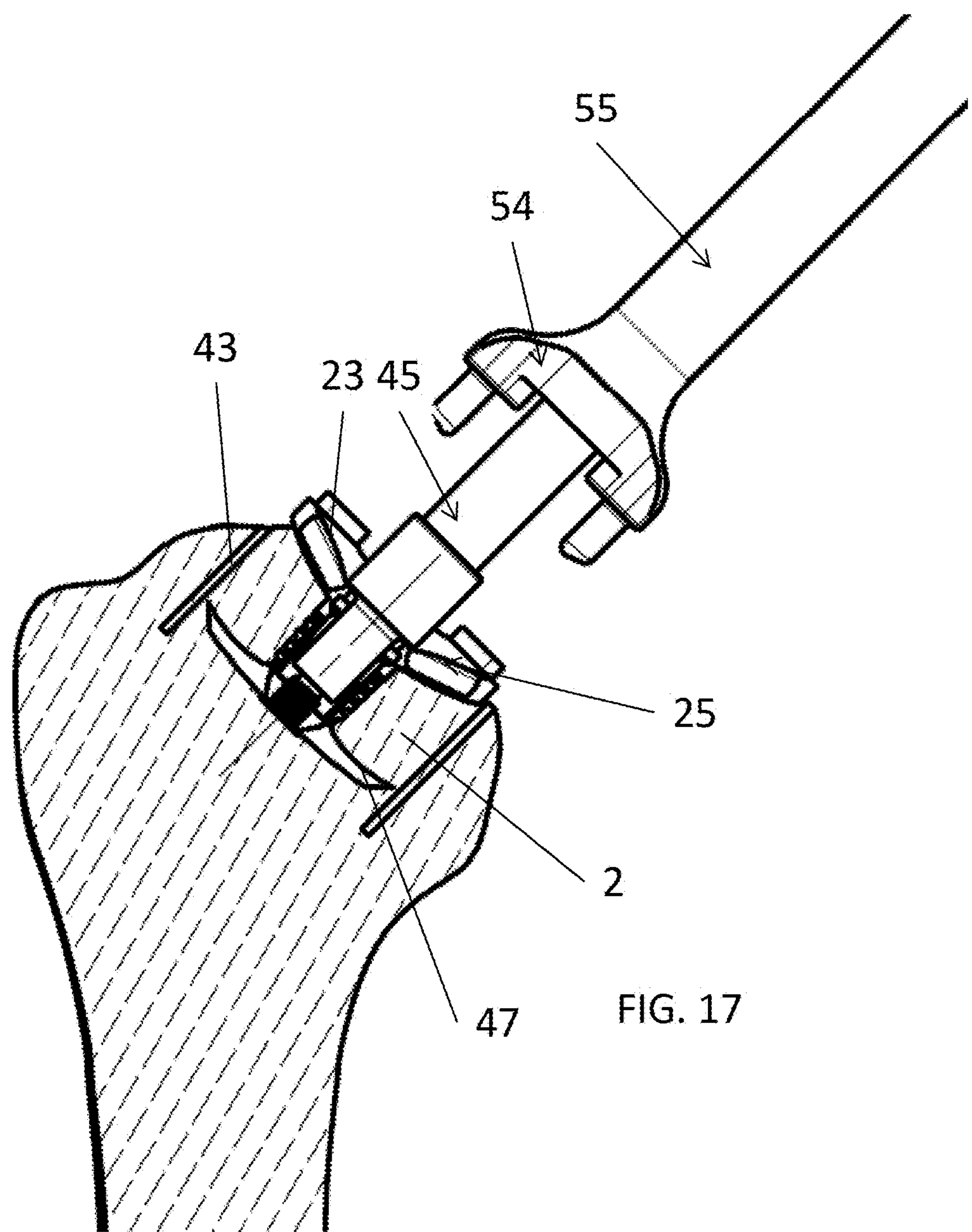
FIG. 17 shows laterally sectioned view of a detail of the bone portion according to FIG. 2 practically at the end of the operating steps of the method according to the invention.
Figure 18:
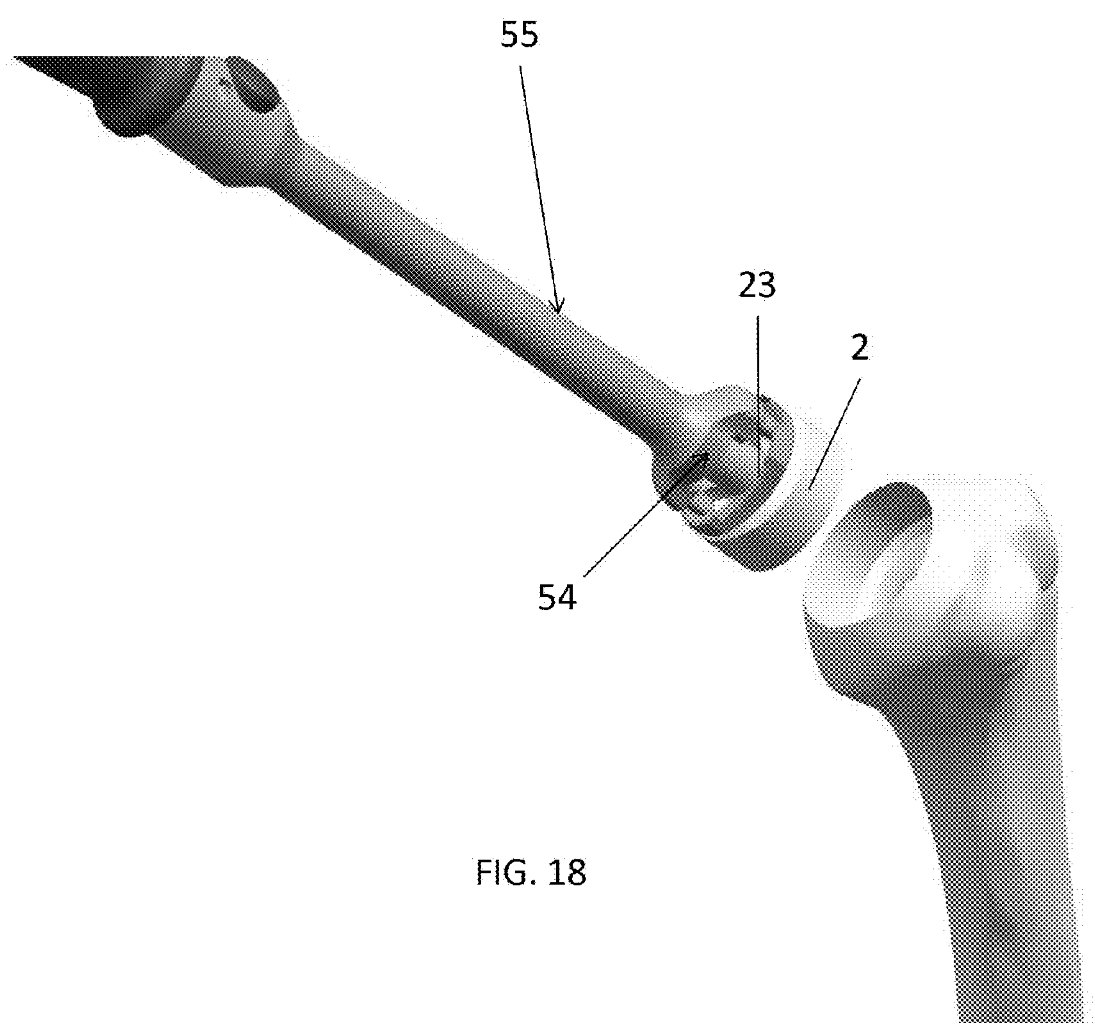
FIG. 18 is a perspective picture view of extraction and removal of an insert performed using the instrument and the method according to the present invention.

This flange 23 is integral with the pin 25 and removal of the insert 2 is performed by engaging the flange 23 using the extractor 55 which can be seen in FIGS. 17 and 18.

Once a circular base 47 of the bone insert 2 has been deep-cut, it is merely required to mill perimetrally the insert using a circular milling cutter circumscribing the flange 23 of the pin element 25 which is fixed to the insert 2 even before the milling operation is performed.

It is entirely clear that, as a result of the instrument and the method according to the present invention, it is possible to reduce and speed up the operating steps designed to remove the bone insert useful for combining with implanted prostheses.

The removal methods are furthermore less invasive than those proposed by the prior art and allow most of the bone material to be conserved and used for the insert to be removed.

The invention claimed is:

1. Instrument for the removal of a bone insert; for example for a shoulder prosthesis, comprising:

- a stem extending along a longitudinal axis and provided with a proximal grip;
- a distal operating head slidably associated with the stem for movement towards and away from each other;
- a cutting element inside said operating head;
- an end tip, projecting coaxially from said operating head; said end tip having a base diameter which is smaller than a diameter of the operating head, said end tip projecting coaxially with the longitudinal axis from the distal portion of the operating head;
- a pushing mechanism, inserted inside said operating head and acting on said cutting element;
- a resilient element which constantly biases the operating head and the stem away from each other, said resilient element being arranged between the operating head and the stem;

wherein said cutting element is entirely curved in form of an arc of a circle and comprises:

- a proximal portion, being a widest portion of the cutting element, slidable inside a matching shape guide formed in said operating head, and
- a tapered blade;

wherein said pushing mechanism is configured to angularly displace the cutting element between:

- a rest position, wherein the tapered blade is concealingly housed inside the end tip of the operating head, and
- an operative position, wherein the tapered blade extends transversely with respect to the longitudinal axis, projecting in a cantilever manner through a side opening in the end tip;
- and wherein said resilient element further biases said cutting element toward said rest position; and
- wherein said pushing mechanism acts on a pin connected to said cutting element, and wherein said pin is perpendicular to said proximal portion, being movable in a longitudinal direction and further slidable along a transverse direction inside a guide slot that is transverse to the longitudinal direction.

2. Instrument according to claim 1, wherein the guide slot is formed at the distal end of the stem.

3. Instrument according to claim 2, wherein the pin projects laterally and perpendicularly from said cutting element.

4. Instrument according to claim 2, wherein said pushing mechanism comprises a distal end of said stem and wherein the pin is associated with said cutting element; said distal end acting on the pin when the stem is moved towards the operating head.

5. Instrument according to claim 2, wherein the distal end of the stem is fork-shaped and engages with the pin via the guide slot and is configured for forcing the cutting element to slide matching shape guide against the action of the resilient element.

6. Instrument according to claim 1, wherein the pin is integral with said proximal portion.

7. Instrument according to claim 6, wherein the cutting element is formed integrally with the pin and projects from a matching seat formed in the operating head under a pushing force of a distal end of the stem.

8. Instrument according to claim 1, wherein said operating head has an essentially cylindrical shape and wherein said matching shape guide comprises a circular-rim guide inside which said cutting element is movably guided.

9. Instrument according to claim 1, wherein said end tip has a frustoconical form.

10. Instrument according to claim 1, wherein said side opening in said end tip is an opening extending along the entire longitudinal extension of said end tip.

11. Instrument according to claim 10, wherein the distal end of the stem has a circular cross-section and diameter smaller than an internal diameter of the operating head and that a spring-loaded means consists of a spring wound around the distal end of the stem.

12. Instrument according to claim 11, wherein the spring extends resiliently inside a variable-extension, cylindrical, annular gap which is defined between an inner edge of the operating head and an edge formed by the smaller diameter of a distal end of the stem.

13. Instrument according to claim 1, wherein said movement of the stem is performed against an action of resilient means.

14. Instrument according to claim 1, wherein said cutting element is shaped as a sickle.

* * * * *